(12) United States Patent
Donaldson et al.

(10) Patent No.: US 12,239,572 B2
(45) Date of Patent: Mar. 4, 2025

(54) WOUND TREATMENT DEVICE

(71) Applicant: Critical Innovations, LLC, Lawndale, CA (US)

(72) Inventors: Ross I. Donaldson, Lawndale, CA (US); Oliver Buchanan, Lawndale, CA (US); Muhammed Hamdan, Lawndale, CA (US); Jonathan Armstrong, Lawndale, CA (US); John Cambridge, Lawndale, CA (US); Nely Cristerna, Lawndale, CA (US)

(73) Assignee: Critical Innovations, LLC, Lawndale, CA (US)

( * ) Notice: Subject to any disclaimer, the term of this patent is extended or adjusted under 35 U.S.C. 154(b) by 0 days.

(21) Appl. No.: 17/876,187

(22) Filed: Jul. 28, 2022

(65) Prior Publication Data
US 2023/0030893 A1 Feb. 2, 2023

Related U.S. Application Data

(60) Provisional application No. 63/227,251, filed on Jul. 29, 2021.

(51) Int. Cl.
*A61F 9/00* (2006.01)
*A61M 35/00* (2006.01)

(52) U.S. Cl.
CPC .......... *A61F 9/0008* (2013.01); *A61M 35/10* (2019.05)

(58) Field of Classification Search
CPC .......... A61F 9/008; A61F 9/0026; A61F 9/04; A61M 35/10
See application file for complete search history.

(56) References Cited

U.S. PATENT DOCUMENTS

| 3,392,725 | A | | 7/1968 | Behney |
| 6,098,628 | A | * | 8/2000 | Funk .......................... A61F 9/04 2/15 |
| 8,672,904 | B1 | * | 3/2014 | Schultz ............... A61M 3/0279 222/541.9 |
| 2002/0124843 | A1 | * | 9/2002 | Skiba ..................... A61M 11/02 128/200.18 |
| 2004/0220537 | A1 | * | 11/2004 | Embleton ............. A61F 9/0008 604/290 |

(Continued)

FOREIGN PATENT DOCUMENTS

| EP | 4124323 A1 | 2/2023 |
| JP | 2007151766 A | 6/2007 |
| WO | 2021011388 A1 | 1/2021 |

OTHER PUBLICATIONS

Chayanin Pratoomsoot et al. A thermoreversible hydrogel as a biosynthetic bandage for corneal wound repair, Biomaterials, vol. 29, Issue 3, 2008, pp. 272-281, ISSN 0142-9612,https://doi.org/10.1016/j.biomaterials.2007.09.031.(https://www.sciencedirect.com/science/article/pii/S0142961207007351 (Year: 2008).*

(Continued)

*Primary Examiner* — Rebecca E Eisenberg
*Assistant Examiner* — Matthew Wrubleski
(74) *Attorney, Agent, or Firm* — Merchant & Gould P.C.

(57) ABSTRACT

An improved method and device are provided for treating wounds. The device generally comprises a wound chamber and/or deployment system. The provided assembly substantially improves wound treatment.

19 Claims, 5 Drawing Sheets

(56) References Cited

U.S. PATENT DOCUMENTS

| | | | |
|---|---|---|---|
| 2008/0066209 A1* | 3/2008 | Kayerod | A45D 44/12 2/9 |
| 2011/0009836 A1* | 1/2011 | Chebli | B65D 47/18 604/298 |
| 2017/0258638 A1* | 9/2017 | Wallis | A61F 9/028 |
| 2017/0266044 A1* | 9/2017 | Lake | A61M 11/00 |

OTHER PUBLICATIONS

Esra Baloglu, Sinem Yaprak Karavana, Zeynep Ay Senyigit & Tamer Guneri (2011) Rheological and mechanical properties of poloxamer mixtures as a mucoadhesive gel base, Pharmaceutical Development and Technology, 16:6, 627-636, DOI: 10.3109/10837450.2010.508074 (Year: 2011).*

National Research Council (US) Subcommittee on Acute Exposure Guideline Levels. Acute Exposure Guideline Levels for Selected Airborne Chemicals: vol. 2. Washington (DC): National Academies Press (US); 2002. 3, 1,1,1,2-Tetrafluoroethane (HFC-134a): Acute Exposure Guideline Levels. (Year: 2002).*

Anthony P. Corfield, Mucins: A biologically relevant glycan barrier in mucosal protection, Biochimica et Biophysica Acta (BBA)—General Subjects, vol. 1850, Issue 1, 2015, pp. 236-252, ISSN 0304-4165, https://doi.org/10.1016/j.bbagen.2014.05.003. (Year: 2015).*

European Patent Office, "European Search Report for Application No. 22187844.0", Jan. 4, 2023, 1-18.

Zentner, G.M., "Biodegradable block copolymers for delivery of proteins and water-insoluble drugs," Elsevier Journal of Controlled Release 72 (2001) pp. 203-215.

* cited by examiner

WOUND TREATMENT DEVICE

RELATED APPLICATION

The present application claims the benefit of U.S. Provisional Application No. 63/227,251, filed Jul. 29, 2021, which is hereby incorporated herein in its entirety by reference.

COMMONLY OWNED APPLICATION

U.S. Patent Publication No. 2020/0022688 titled Systems and Methods Relating to Medical Applications of Synthetic Polymer Formulations, having at least one of the same inventors, is hereby incorporated by reference herein in its entirety.

This invention was made with government support under contract W81XWH-21-9-0003, "Eye-Aid System for Acute Ocular Injuries," awarded by U.S. Army Medical Research Acquisition Activity (USAMRAA). The government has certain rights in the invention.

FIELD OF THE INVENTION

The present disclosure relates generally to the medical field, and more particularly, to systems and methods for wound treatment. In one application, the present disclosure relates to systems and devices for delivering treatment to the eye and/or its surrounding structures.

BACKGROUND OF THE INVENTION

A wide variety of diagnostic and/or therapeutic procedures involve the delivery of wound healing solutions to the body. Potential objectives include the delivery of pharmaceutical agents and/or compounds with beneficial properties for wound healing (e.g. hemostatic agents, antibiotics, anesthetics, analgesics, antifungals, environmental stabilizers, antimicrobials, regenerative agents, immune modulation agents, antibiofilm agents). Wounds can have occurred to many parts of the body, including ocular and/or peri-ocular tissues.

The management of undifferentiated ocular injuries in the out-of-hospital arena is a significant medical problem. One issue is the difficulty of diagnosing specific injuries during initial prehospital care due to lack of provider training, diagnostic equipment, and treatment modalities. For example, the national standard curriculum for EMT-Basics does not have a dedicated lecture on the diagnosis and treatment of orbital trauma.

This problem is shared by the US military, where ocular injuries at Role 1 (i.e. near the point of injury), including full-thickness corneal and corneoscleral wounds, is a major problem. Although 10-15% of combat-related trauma involves eye injury, there currently exists limited management options for the far forward medical provider (e.g. medic, physician's assistant) at Role 1. Current Tactical Combat Casualty Care (TCCC) guidelines consist simply of covering the eye with a rigid eye shield, administration of oral antibiotics, and transfer to the next level of care. As such, it must be assumed that the average far forward provider does not have the training or tools to make specific ophthalmologic diagnoses, among the large differential of orbital and periorbital trauma that includes caustic keratoconjunctivitis, conjunctival hemorrhage, conjunctival laceration, corneal abrasion, corneal laceration, globe rupture, iridodialysis, lens dislocation, ocular foreign body, orbital fracture (e.g. frontal sinus fracture, naso-ethmoid fracture, inferior orbital wall fracture, medial orbital wall fracture), posterior vitreous detachment, retinal detachment, retrobulbar hemorrhage/hematoma, ocular compartment syndrome, subconjunctival hemorrhage, traumatic hyphema, traumatic iritis, traumatic mydriasis, traumatic optic neuropathy, vitreous detachment, vitreous hemorrhage, ultraviolet keratitis, corneal ulcer, endophthalmitis, eyelid injury, lacrimal system injury, periorbital trauma, and full-thickness corneal and corneoscleral injuries. Thus, proposed solutions that require such a provider to directly apply treatment to a specific orbital laceration site or otherwise manipulate the eye are unlikely to succeed and are potentially harmful at Role 1.

Thus, both for civilian and military emergency medical services (EMS) providers, initial ocular trauma and other eye complaint care is frequently simply the placement of a protective shield (i.e. Fox Eye Shield) and transport to the next level of care. While this prevents additional injury, it has no therapeutic benefits and fails to significantly stabilize injured tissues, stop bleeding, prevent infection, or halt harmful extravasation of ocular contents. Even once reaching the next role of care (for the military) or the emergency department (for civilian care), there lacks a current technology for stabilizing more severe ocular injuries (e.g. full-thickness corneal and corneoscleral wounds) until time of definitive care, frequently by an ophthalmological specialist.

The literature discloses various additional known methods and devices for wound treatment devices, including those for ocular and peri-ocular problems.

For example, there are many variations on eye protective devices before and/or after injury. These range from sunglasses, swim goggles, masks, and related devices, well known in the art. Additionally, for treatment of eye injury, there are many variations on eye patches (e.g. Fox eye shield). This includes U.S. Pat. Pub. No. 4,862,902 to Goffman that describes a classic eye protector with adhesive for attachment to the face; U.S. Pat. No. 4,677,974 to Leonardi that has a strap to hold it onto the face and a pad to place pressure on the eye; U.S. Pat. No. 5,004,333 to Bruhl, Jr. that is a classic rigid eye patch with holes that the user tapes or other attaches to the face; U.S. Pat. No. 10,821,025 B1 to Stravitz that describes a rigid eye patch with holes and spaces for alternative taping; 2011/0034849 A1 to Cooks that has a flexible protector; U.S. Pat. No. 4,709,695 to Kohn et al. that includes a Velcro portion that can be removed and reattached; and, U.S. Pat. No. 8,708,982 B2 to Lin that describes a wound chamber that can open and close. However, these rigid eye protectors provide their benefit from prevention of additional trauma to the wound and/or eye, without direct delivery of therapeutic agents and/or components to treat the current trauma.

Other examples seek to retain moisture within the wound, periorbital tissues, and/or eye. These include U.S. Pat. Pub. Nos. 2008/0148461 A1 to Guyuron et al. that describes a moisture retaining eye cover; 2004/0074502 A1 to Abbasi that describes eye patches for anesthesia to maintain eye closure during surgery; and U.S. Pat. No. 5,740,550 to Yavitz that describes an eye patch for retaining moisture with a contact lens over it. However, these only maintain existing fluids around the wound and/or eye, without direct delivery of additional therapeutic agents and/or components.

Other examples include devices tailored to provide negative pressure to wounds and/or eyes. These include U.S. Pat. Pub. Nos. US 2018/0235814 A1 to Eriksson et al and U.S. Pat. No. 6,960,181 B2 to Stevens that describe negative pressure wound chambers. However, negative pressure is not appropriate for all wounds, especially ocular wounds that may have a ruptured globe.

There are also devices that can deliver wound healing agents. This includes U.S. Pat. No. 8,672,904 B1 to Schultz that describes a splash shield system for attachment onto a sterile fluid bottle for delivery of fluid directly to eye tissues. However, this is not a standalone wound and/or eye chamber and delivers only bottle-based fluids.

This additionally includes U.S. Pat. Pub. No. 6,098,628 to Funk that describes a vented eye shield device that additionally can allow delivery of medications to ocular tissues. Similarly, U.S. Pat. Pub. No. 4,473,370 to Weiss describes an occlusive eye shield for holding in fluids around the orbit. However, these devices do not allow delivery of foaming agents and, if used for such, could cause significant increases in intraocular pressures that are contraindicated when globe rupture is a potential concern. Additionally, these devices do not allow delivery of therapeutic agent that stabilize injured tissues while providing other beneficial wound healing properties.

Regardless of use, the wound treatment devices and methods of the art have not before provided for an optimized device for providing optimized treatment of wounds, including ocular and/or peri-ocular wounds. As such, there is a need for a device and method to do so.

Each of the patents and published patent applications mentioned above are hereby incorporated by reference herein.

SUMMARY OF THE INVENTION

The present disclosure overcomes and substantially alleviates the deficiencies in the prior art by providing improved systems and methods relating to wound treatment.

Under many embodiments, the present disclosure can provide a solution to the problem of undifferentiated ocular injury, including full-thickness corneal and corneoscleral wounds of various shapes and sizes. Embodiments disclosed herein can benefit or, at the very least, do no harm to the wide spectrum of potential eye injuries, while stabilizing, sealing, and/or preserving ocular tissues. Embodiments of the present disclosure can be simple and quick to use by first aid personnel, without preparation time or complicated administration processes. Embodiments of devices disclosed herein can also be simple to store (e.g. stable in a wide range of environmental extremes; shelf life ≥2 years) and transport (e.g. small, lightweight, durable), making them particularly well-suited for expeditionary use.

Embodiments of the present disclosure can easily be applied to an injured patient in an austere setting, following instructions for use similar to currently approved treatment protocols and without need for extra equipment, thus minimizing additional training and materiel requirements.

Under some embodiments, to utilize the device the provider:
1. Removes the nonstick backing,
2. Positions the eye shield on the patient (e.g. using device adhesive),
3. Delivers a therapeutic agent (e.g. deployment of a foaming synthetic polymer), and
4. Disconnects the tubing, if so desired for ambulation or transport.

Embodiments of the present disclosure can gently spread topically over eye tissues. Under some embodiments, the device can be reapplied multiple times, if necessary. Under many embodiments, the system is specifically designed to always prevent placement of additional pressure on the eye, which is strongly contra-indicated in patients with possible globe rupture. Under many embodiments, it is also designed to overcome provider hesitancy in manipulating the injured eye; such handling is another potential cause of increased intraocular pressure. Under many embodiments, there is no need to open and/or evert the eyelid, as the foam gently fills the space around the injured eye and will naturally spread to cover its anterior portion (e.g. skin, eyelid, cornea, and sclera), including around prolapsed ocular structures and foreign bodies, when present.

Embodiments of the present disclosure can work by dispensing a thermosensitive hydrogel gel and/or foam specifically engineered to solidify as it warms in contact with the skin. This means that it becomes liquid when chilled, but returns to a solid gel when warmed near skin temperature (i.e. the opposite of most substances). Under many embodiments, the pressure change associated with deploying a canister of the present invention causes a transient temperature-drop (e.g. much like opening a can of soda) that temporarily liquifies the hydrogel to allow its easy deployment as a gentle foam. Once deployed on the eye, it then quickly warms to rapidly become a transparent, self-setting, hydrogel sheet dressing.

Embodiments of the present disclosure can dispense a self-setting, thermoresponsive, hydrogel foam. Under many embodiments, foaming more easily spreads to cover irregular and amorphous surfaces (e.g. around prolapsed ocular structures), before setting into a solid structure that preserves, physically supports, and/or otherwise stabilizes injured ocular tissues, which under many embodiments include full-thickness corneal and corneoscleral wounds of various shapes and sizes. Under many embodiments, this seals possible corneal and/or corneoscleral injuries to prevent additional leakage and maintain healthy intraocular pressure levels, while being safe for the full spectrum of possible traumatic eye pathology.

Embodiments of the present disclosure can also have multiple additional benefits of utility to the far forward provider. Under many embodiments, the foaming polymer of the present invention has an intrinsic ability to prevent bacterial adhesion and biofilm formation. Under many embodiments, the foam also provides irrigation-like active cooling to the eye. Under some embodiments, this foam has fire extinguishing properties (e.g. for use immediately after a burn or blast injury).

Under some embodiments, the foam provides a means to deliver to potentially poorly perfused tissues very high local concentrations of pharmaceutical or related agents. Under various embodiments, this includes one or more of the following: analgesics, anesthetics, antimicrobials, antifungals, environmental stabilization agents, hemostatics, regenerative agents, immune modulation agents, preservatives, and/or buffer solutions. Examples of such agents include lidocaine, bupivacaine, thymol, nystatin, terbinafine, phosphate buffered saline, tranexamic acid, coagulation factors, nerve regenerative agents, and growth factors. Under some embodiments, the foam is sterile. Under some embodiments, the foam contains preservatives (e.g. benzalkonium chloride, phenoxyethanol).

Under some embodiments, antimicrobials include one or more antibiotics (e.g. cephalosporins, aminoglycosides, glycopeptides, fluoroquinolones). Under some embodiments, these antibiotics are selected to prevent and/or treat orbital infections. Under many embodiments, the local concentrations of the agents overcome drug-resistance mechanisms in multidrug-resistant strains. Under some embodiments, the antimicrobials are at standard antibiotic concentrations for eyedrops and/or other eye preparations that are well known in the art. Under some embodiments, the antibiotic concentrations are "fortified" (i.e. higher than standard preparations) prevent and/or treat more severe infections and/or overwhelm dose-related drug-resistance mechanisms.

Under some embodiments fortified antibiotic concentrations include, but are not limited to, the many well known to practitioners in the art. Examples include aminoglycosides, for example tobramycin 14 mg/ml (1.4%), gentamicin 14 mg/ml (1.4%), amikacin 20 mg/ml; amikacin 30 mg/ml; amikacin 40 mg/ml; cephalosporins for example cefazolin 50 mg/ml (5%); ceftazidime 50 mg/ml (5%); and, fluoroquinolones such as moxifloxacin 5 mg/mL (5%) and ciprofloxacin 0.3%. Other examples include vancomycin 10 mg/mL (1%); vancomycin 25 mg/mL (2.5%); vancomycin 40 mg/ml (4%); vancomycin 50 mg/ml (5%); linezolid 2 mg/ml (0.2%); colistin (0.19%); imipenem-cilastatin (1%); bacitracin 10,000 IU; clarithromycin 10 mg/ml; azithromycin 10 mg/ml; sulfacetamide 100 mg/ml; and trimethoprim/sulfamethoxazole 16-80 mg/ml. Additionally, potential agents include antifungals such as amphotericin B (0.15%) and voriconazole (1%).

Embodiments of the present disclosure can treat undifferentiated ocular injuries, including full-thickness corneal and corneoscleral wounds. Under many embodiments the present disclosure is specifically engineered knowing that significant eye injuries will require repeat examinations as the patient moves up the roles of care (e.g. initial Role 1 medic/physician assistant; Role 2 general physicians/surgeons; Role 3 ophthalmologist; Role 4 sub-specialist). Non-transparent dressings and other solutions that irreversibly adhere to tissues are thus contraindicated in this setting. Under many embodiments, the eye shield and/or solidified hydrogel of the present invention are fully see-through, thus allowing easy patient reexamination while simultaneously protecting the eye from additional trauma. Under many embodiments, when removal is indicated (e.g. by the terminal ophthalmologist), unlike standard hydrogel products the hydrogel of the present invention is thermoreversible and easily eliminated by application of room-temperature and/or cold liquid (e.g. cooled water), facilitating easy ejection from complex eye wounds. Under many embodiments, it is also naturally resorbable by the body, should it become embedded in eye tissues. Under many embodiments, it can be left in place or reapplied for multiple days without issue.

Under many embodiments, the device includes a means for attaching to the patient. Embodiments include various temporary medical adhesives well known in the art (e.g. hydrogel, acrylate-based hydrogel). Some of these embodiments include a nonstick backing (e.g. that can be removed by the user before placement on the patient). Some embodiments include a compliant layer (e.g. foam layer) to provide a soft surface and/or allow the device to better contour to the patient's face. Under some embodiments, this compliant layer is a closed-cell and/or open-cell foam. Some embodiments include a strap, temple, or other component to attach the device in a non-adhesive manner.

Under many embodiments, the device delivers a therapeutic agent from a holding chamber, syringe, and/or canister to the wound area (e.g. a periocular chamber). Under some embodiments, the therapeutic agent is dispensed through a tubing and/or other mechanism connecting the canister to the eye shield (e.g. with or without luer connection(s)). Under some embodiments, this therapeutic agent is water (e.g., "tap water"). Under some embodiments, this therapeutic agent is a standard medical fluid, with or without additional substances, such as 0.9% normal saline, other percent saline (e.g. 0.45%, 3%), sterile water, D5W, D10W, D50W, or another fluid well known in the art.

Under some embodiments, the therapeutic agent delivered is not under pressure. Embodiments of therapeutic agents not under pressure include liquids and/or gels. Under some embodiments, the therapeutic agent delivered is under pressure. Embodiments of therapeutic agents under pressure include foams, gases, and/or gaseous mixtures. Canisters for delivering substances under pressure are well known in the art and different embodiments utilize different types of expansion tanks, which under some embodiments contain one or more of the following features: aerosol, screw-on, easy click on, pierceable. These deliver the therapeutic agent in a pre- and/or post-foaming gel configuration. Under several embodiments, these canisters contain one or more propellent gases, as is well established in the art. Under several embodiments, the propellent gas is kept separate from the polymer to be delivered by a membrane, piston, and/or bag, so that it can transmit pressure but does not directly mix with the agent to be delivered to the body.

Under some embodiments, the therapeutic agent delivered is a synthetic polymer formulation, with or without additional substances. Under various embodiments, the synthetic polymer formulation is a foam that gently expands once reaching the wound and/or wound chamber. Under some of these embodiments, the material does not need to chemically react on the wound, rather its innate properties and/or a propellant pushing the material causes it to expand once reaching the desired space. The polymer formulation expands to partially or fully fill the area around the wound and/or wound chamber. Embodiments of the present disclosure can provide a moist hydrating environment, which prevents corneal desiccation (e.g. from lid injuries or other exposure). Under many embodiments, the dispensed agent is oxygen permeable. Under many embodiments, the device is engineered so as to prevent significant pressures from building up during delivery (e.g. multiple vents from the system). Under various embodiments, the system allows controlled agent to be delivered and/or maintained to a selected body area by the user (e.g. under manual and/or automated control).

Under many embodiments, the system delivers substances to provide wound healing benefits. Many of the embodiments of the present disclosure provide hemostatic properties either through polymer properties and/or additional pharmaceutical agents (e.g. tranexamic acid). Some embodiments of the present disclosure contain one or more additional substances increase polymer viscosity and/or to assist with preventing, slowing, and/or stopping bleeding and/or fluid leakage (e.g., aqueous fluid, vitreous fluid). These include, but are not limited to, components of the intrinsic clotting pathway (e.g. factors XI, IX, VIII); components of the extrinsic clotting pathway (e.g. transmembrane receptor tissue factor, plasma factor, factor VII/VIIa); tranexamic acid and other amino acids and their analogs; epinephrine and other vasoconstrictors; thrombin; fibrinogen; potassium ferrate; cellulose, including oxidized and/or regenerated cellulose; kaolin; smectite granules; zeolite; chitosan; sodium carboxymethylcellulose; amylopectin; microfibrillar collagen; propyl gallate; aluminum sulfate; fully acetylated poly-N-acetyl glucosamine; related substances; and other clotting agents, platelet aggregators, and substances that reduce or stop bleeding. Other examples of additional substances include: cellulosics, for example, hydroxyethyl cellulose, hydroxypropyl cellulose, methyl cellulose, hydroxypropyl methylcellulose, hydroxyethyl methyl cellulose, and other similar compounds; chitosans, for example, chitosan lactate, chitosan Salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine Substituted chitosan and salts thereof; alginates, for example, sodium alginate, potassium alginate, magnesium alginate, calcium alginate, aluminum alginate, and other known alginates.

Some embodiments of the present disclosure can contain one or more additional substances to assist with preventing, slowing, and/or stopping bacterial and/or other infections. These include, but are not limited to, antimicrobial agents (e.g. antibiotics), disinfectants (e.g. alcohols, aldehydes, oxidizing agents, phenolics, quaternary ammonium compounds, silver-based products, copper-based produces, and/or other disinfectants), and/or other agents (e.g. antifungals). Under some embodiments, a synthetic polymer with one or more of these additional substances is delivered into a body cavity. Under other embodiments, a synthetic polymer with one or more of these additional substances is sprayed or otherwise delivered to an external wound or area.

Under some embodiments, one or more additional substance also provides analgesic and/or anesthetic capabilities (e.g. from sealing corneal, scleral, and other injured nerve endings; from added pharmaceuticals). Embodiments include the many known substances in this category known in the art, including local anesthetics such as benzocaine, procaine, chloroprocaine, lidocaine, prilocaine, tetracaine, bupivacaine, cinchocaine, and/or ropivacaine.

Various embodiments of the present disclosure can have one or more of the following characteristics in any combination: it is field-adapted with a small size, easily fitting into a medical field kit; it has a delivery device for safe and rapid deployment by medics or other providers; it is stable without need for refrigeration, with the ability to maintain activity under the environmental extremes experienced in military operations; it is rapidly applied to penetrate wound injuries of all shapes and sizes; it induces hemostasis; it provides a delivery mechanism for a wide range of additional bioactive clotting agents; it prevents bacterial adhesion and/or biofilm formation; it inhibits drug-resistance mechanisms in multi-drug-resistant strains of bacteria; it is partially or fully resorbable by the body; it has a low risk of complications; it is not exothermic and/or has minimal risk of iatrogenic thermal injury to organs; it is transparent does not discolor the wound; it is water soluble; it may be quickly and easily washed away for easy removal if needed for emergent laparotomy surgery; it contains no toxic substances or materials with potential for adverse environmental effects; it uses expanding and/or propellant components that are non-ozone depleting; and/or it is made in whole or part from synthetic, inert polymers that are already FDA and EU-approved for pharmaceutical applications.

Several embodiments of the present disclosure can deliver to the wound and/or wound chamber a synthetic polymer formulation as described in U.S. Patent Publication No. 2020/0022688, previously incorporated by reference herein.

Under some embodiments, the synthetic polymer formulation consists of polymer (e.g. P407 and/or P188), phosphate buffer system, and/or expanding gas (e.g. HFC134 and/or AFA1234Z). Under some embodiments, the synthetic polymer formulation includes a preservative (e.g. phenoxyethanol).

Under some embodiments, the device comes sterile. Examples of processes used to make all or some of the components sterile include e-beam, x-ray, other radiation, and/or ethylene oxide.

Under many embodiments, the pH of the therapeutic agent is around 7.0 (e.g. 6.0-8.0) and/or does not sting and/or cause tearing in the eyes.

While particular embodiments of the invention have been described, it is not intended that the invention be limited thereto, as it is intended that the invention be as broad in scope as the art will allow and that the specification be read likewise.

From the foregoing, it can be seen that the present invention provides an effective means for treating wounds (e.g. ocular, periocular) within animals, especially humans. Although the example of ocular and/or periocular wounds has at times been used to illustrate the invention, it should not limit its scope as it could also similarly be used to treat other wounds on the body.

Moreover, it should also be apparent that the device can be made in varying lengths, sizes and capacities, and the precise composition of the device may be varied appropriately to treat adults, children, and infants. While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification and that elements of certain embodiments can be combined with elements of other embodiments. Additional objects, advantages, and novel features of the invention will be set forth in the description which follows, and will become apparent to those skilled in the art upon examination of the following detailed description and figures. It should be understood that not all of the features described need be incorporated into a given system or method.

DETAILED DESCRIPTION OF THE INVENTION

Figure 1:
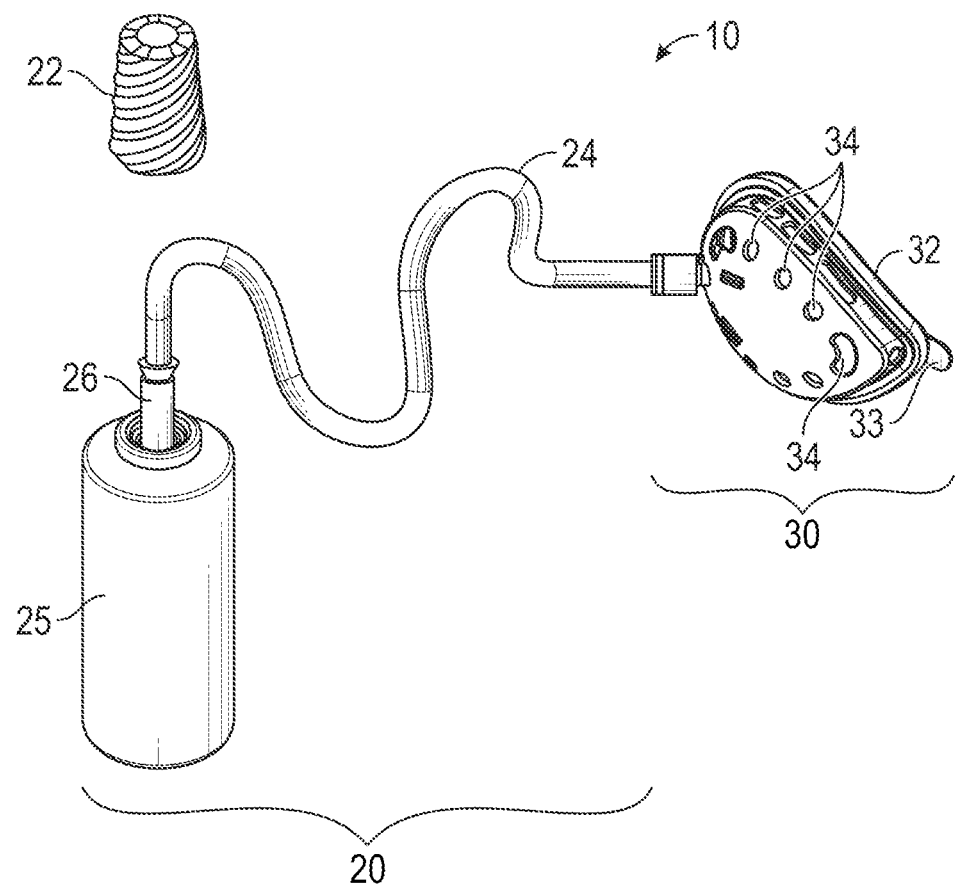
FIG. 1 is an isometric view depicting a wound treatment device in accordance with an embodiment of the disclosure, as assembled prior to use.

Referring to the drawings FIG. 1-6, embodiments of the present disclosure are illustrated.

FIG. 1 shows wound treatment device 10 made up of deployment system 20 and eye shield assembly 30 according to an embodiment. Under this embodiment, wound treatment device 10 allows a user to deploy the system's therapeutic agent (e.g. foaming synthetic polymer) onto the periorbital and/or orbital area of an injured patient (not shown). To do so, the user first assembles the system by removing cap 22 and reversibly connecting tubing 24 to eye shield assembly 30. The user then removes nonstick backing 32 from eye shield assembly 30 by utilizing nonstick backing tab 33. Eye shield assembly 30 is then positioned onto the patient, such that its adhesive area adheres to the periorbital area around the patient's injured eye. These two first steps may be reversed under some embodiments, such that tubing 24 is connected to eye shield assembly 30 after eye shield assembly 30 has been placed upon the patient, depending on caregiver preference and/or user characteristics.

The user next deploys the system's therapeutic agent (e.g. foaming synthetic polymer) by, under this embodiment, pushing on canister adapter 26 of canister 25 to deliver therapeutic agent to the patient. The therapeutic agent travels from inside canister 25 through tubing 24 to eye shield assembly 30. Eyelets 34 allow excess therapeutic agent (e.g. gas and polymer) to leave the inside chamber of eye shield assembly 30 without allowing significant buildup of pressure to damage the patient's eye underneath (not shown).

After deployment, the user may disconnect tubing 24, if so desired, to facilitate patient ambulation and/or transport.

Figure 2:
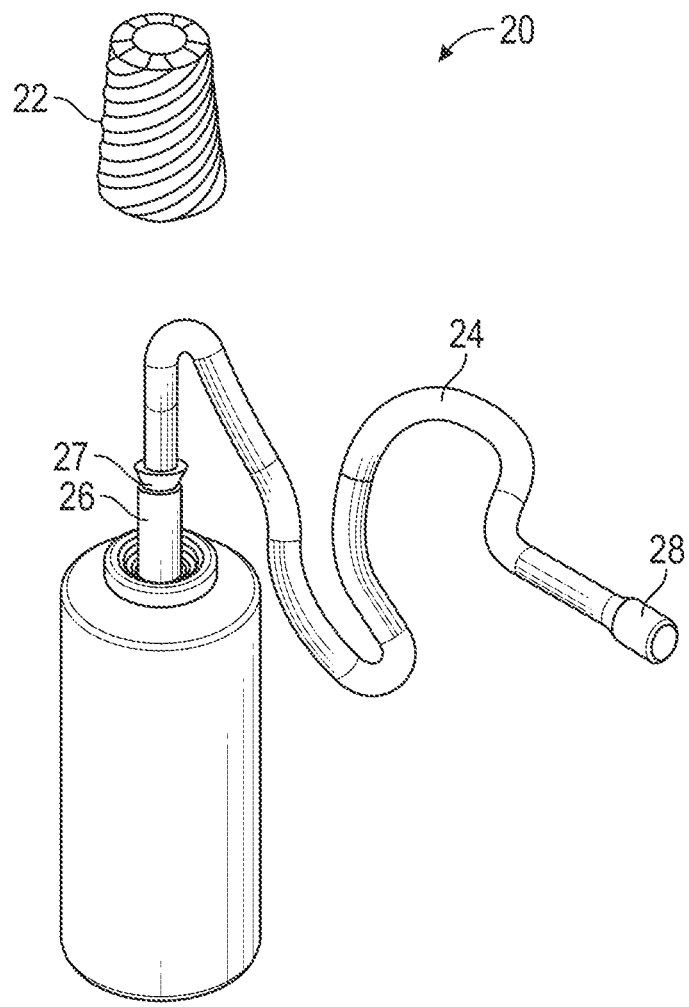
FIG. 2 is an isometric view of a deployment system 20 in accordance with an embodiment of the disclosure.

Referring now to FIG. 2, one embodiment of deployment system 20 is shown. In this embodiment, cap 22 has been removed and tubing 24 connected to canister adapter 26 via female luer lock 27. Under many embodiments, cap 22 has a means for determining if it has been previously opened (i.e. tampered with). Under some embodiments, there is an additional seal to maintain sterility within cap 22 until use. On the other end of tubing 24 is male luer lock 28, which can connect to eye shield assembly 30 (not shown in this figure).

Figure 3:
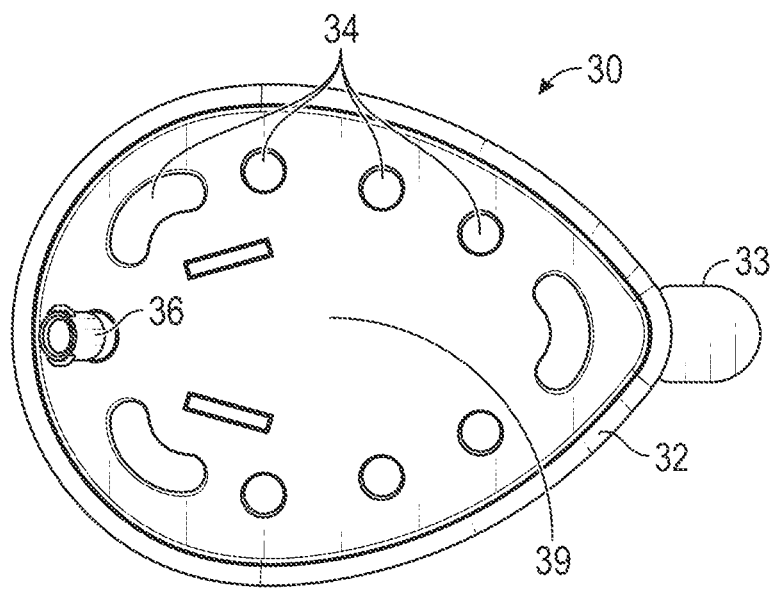
FIG. 3 is a top view of an eye shield assembly 30 in accordance with an embodiment of the disclosure.
Figure 4:
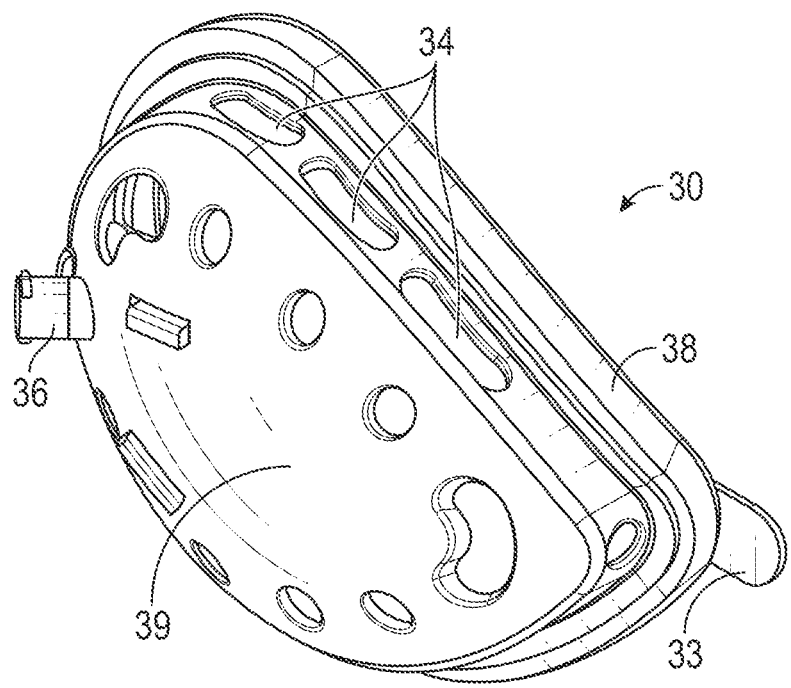
FIG. 4 is an isometric top view of an eye shield assembly 30 in accordance with an embodiment of the disclosure.

Referring now to FIGS. 3-4, one embodiment of eye shield assembly 30 is shown via top views. The female eye shield luer lock 36 allows reversible connection to male luer lock 28 and tubing 24 (both not shown in these figures) to allow polymer delivery to the inner chamber of eye shield assembly 30 and thus the patient. Eyelets 34 allow gas and excess polymer to leave the inside chamber of eye shield assembly 30 without allowing significant buildup of pressure to damage the patient's eye underneath (not shown). Nonstick backing tab 33 allows the user to remove nonstick backing 32 from eye shield assembly 30 to expose adhesive to connect the device to a patient. Foam layer 38 provides a soft surface to allow the device to contour to the patient's face, while connecting the transparent eye shield 39 to the lower adhesive layer (not shown).

Figure 5:
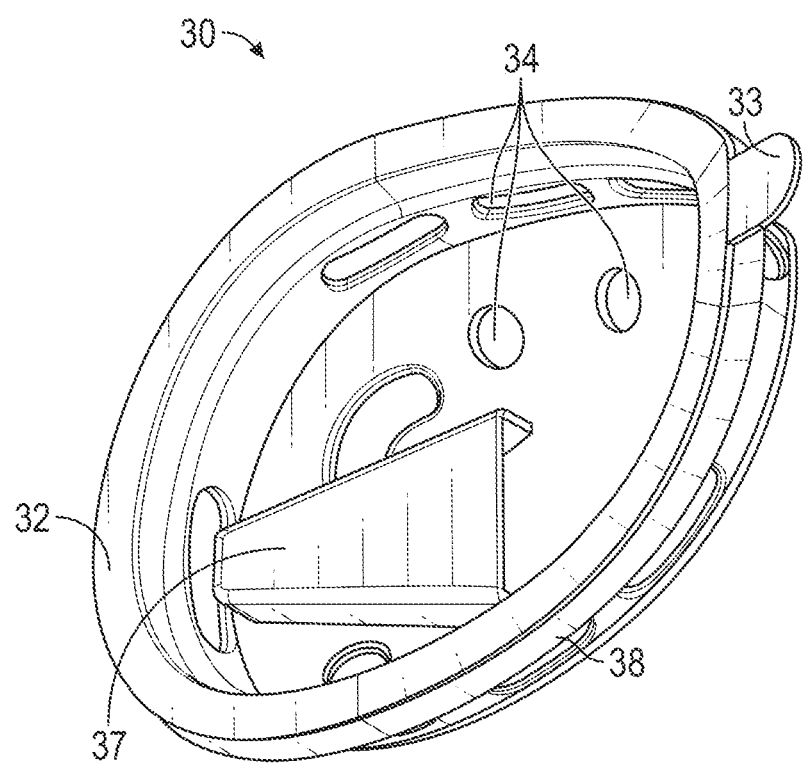
FIG. 5 is an isometric bottom view of an eye shield assembly 30 in accordance with an embodiment of the disclosure.
Figure 6:
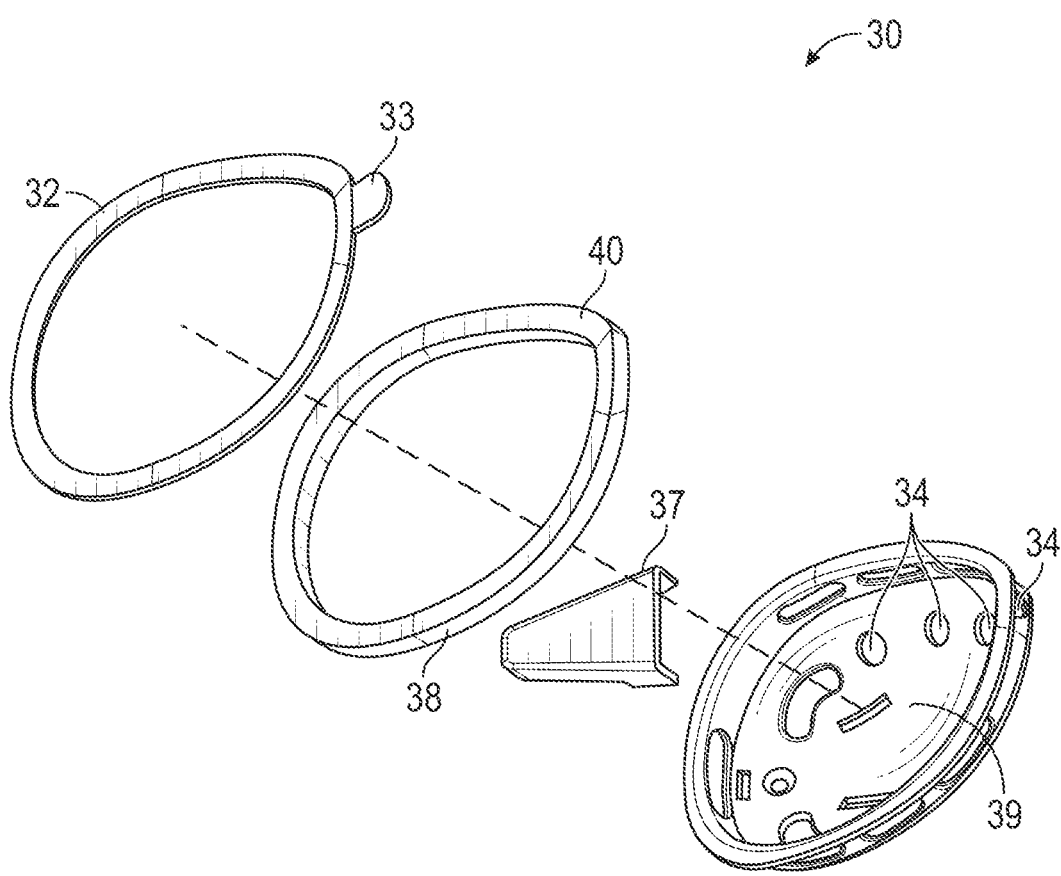
FIG. 6 is an exploded bottom view of an eye shield assembly 30 in accordance with an embodiment of the disclosure.

Referring now to FIGS. 5-6, one embodiment of eye shield assembly 30 is shown via bottom isometric views. Nonstick backing 32 can be removed by the user via nonstick backing tab 33. Eyelets 34 allow direct connection between the inner chamber of eye shield assembly 30 and the external environment. Diffuser 37 ensures that foam delivered into the chamber is appropriately spread over the patient's orbital and periorbital structures within it, while minimizing the pressure delivered to these areas. Foam layer 38 provides a soft surface to allow the device to contour to the patient's face, while connecting eye shield 39 to adhesive layer 40. FIG. 6 shows an exploded view of the separate layers of eye shield assembly 30 (e.g. during manufacture). Under many embodiments, the therapeutic agent is delivered gently enough that there is no need for diffuser 37, which is not present in those embodiments.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An ocular and/or periocular wound treatment device, comprising:
 a deployment system initially containing a therapeutic agent and including tubing configured to connect the deployment system to an eye shield assembly;
 an eye shield assembly, the eye shield assembly including:
  a means for attachment to a patient with a temporary adhesive
  at least one raised connector extending upwardly from the eye shield assembly configured to connect to the tubing, the raised connector defining an aperture through the eye shield assembly through which the therapeutic agent is configured to be delivered through the eye shield assembly, and
  one or more passages to allow gas to escape, the one or more passages being planar openings through the eye shield assembly at different locations than the aperture through which the therapeutic agent is configured to be delivered through the eye shield; and
 wherein the device may continuously remain in place during and after therapeutic agent delivery with the one or more passages allowing gas to escape from the eye shield assembly to prevent buildup of pressure in the eye shield from damaging the patient's eye,
 wherein the therapeutic agent comprises a thermoreversible polymer formulation including a poloxamer.

2. The wound treatment device of claim 1, where the eye shield assembly further comprises at least one luer connector.

3. The wound treatment device of claim 1, wherein the temporary medical adhesive comprises a hydrogel adhesive.

4. The wound treatment device of claim 1, wherein the eye shield assembly further comprises a nonstick backing.

5. The wound treatment device of claim 1, wherein the eye shield assembly further comprises a compliant layer to provide a soft surface and/or allow the device to better contour to the patient's face.

6. The wound treatment device of claim 5, wherein the compliant layer comprise a foam layer.

7. The wound treatment device of claim 1, wherein the deployment system further comprises a cap configured to indicate if the deployment system has been previously opened.

8. The wound treatment device of claim 1, wherein the device is provided sterile.

9. A method of treating an ocular and/or peri-ocular wound, comprising:
removing a nonstick device backing from an eye shield;
positioning the eye shield on a patient with an adhesive;
delivering a therapeutic agent from a canister to the patient through the eye shield via tubing; and
leaving the eye shield in place during and after therapeutic agent delivery, and wherein the eye shield includes one or more passages that allow gas to escape from the eye shield to prevent buildup of pressure in the eye shield from damaging the patient's eye, the one or more passages being different openings than the aperture through which the therapeutic agent is delivered,
wherein the therapeutic agent comprises a thermoreversible polymer formulation including a poloxamer,
wherein the thermoreversible polymer formulation comprises an alginate configured to increase viscosity of the thermoreversible polymer formulation and/or to assist with preventing, slowing and/or stopping bleeding and/or fluid leakage.

10. The method of claim 9, further comprising disconnecting the tubing after delivering the therapeutic agent to facilitate ambulation, transport, and/or patient comfort.

11. The method of claim 9, wherein the method includes using at least one luer connector to allow therapeutic agent deployment.

12. The method of claim 9, wherein the method includes spreading the therapeutic agent topically over tissue.

13. The method of claim 9, wherein the poloxamer is at least one of P407 and P188.

14. The method of claim 9, wherein the thermoreversible polymer formulation includes a buffer system.

15. The method of claim 14, wherein the buffer system produces the thermoreversible polymer formulation with a pH between 6.0 and 8.0.

16. The method of claim 9, wherein the thermoreversible polymer formulation includes an expanding gas.

17. The method of claim 16, wherein the expanding gas is at least one of HFC134 and AFA1234Z.

18. The method of claim 9, wherein the thermoreversible polymer formulation includes a preservative.

19. A method of treating an ocular and/or peri-ocular wound, comprising:
removing a nonstick device backing from an eye shield;
positioning the eye shield on a patient with an adhesive;
delivering a therapeutic agent from a canister to the patient through the eye shield via tubing; and
leaving the eye shield in place during and after therapeutic agent delivery, and wherein the eye shield includes one or more passages that allow gas to escape from the eye shield to prevent buildup of pressure in the eye shield from damaging the patient's eye,
wherein the therapeutic agent comprises a thermoreversible polymer formulation including:
a poloxamer,
an alginate configured to increase viscosity of the thermoreversible polymer formulation and/or to assist with preventing, slowing and/or stopping bleeding and/or fluid leakage,
a buffer system,
an expanding gas, and
a preservative.

* * * * *